(12) United States Patent
Lee

(10) Patent No.: US 12,114,848 B2
(45) Date of Patent: Oct. 15, 2024

(54) SURGICAL INSTRUMENT FOR REPAIRING CARTILAGE TEAR

(71) Applicant: AJU PHARM. CO., LTD, Seoul (KR)

(72) Inventor: Jin Kwon Lee, Seoul (KR)

(73) Assignee: AJU PHARM. CO., LTD, Seoul (KR)

( * ) Notice: Subject to any disclaimer, the term of this patent is extended or adjusted under 35 U.S.C. 154(b) by 401 days.

(21) Appl. No.: 17/638,901

(22) PCT Filed: Jul. 15, 2020

(86) PCT No.: PCT/KR2020/009350
§ 371 (c)(1),
(2) Date: Feb. 28, 2022

(87) PCT Pub. No.: WO2021/049746
PCT Pub. Date: Mar. 18, 2021

(65) Prior Publication Data
US 2022/0304671 A1    Sep. 29, 2022

(30) Foreign Application Priority Data
Sep. 10, 2019    (KR) ........................ 10-2019-0112007

(51) Int. Cl.
*A61B 17/04*    (2006.01)
(52) U.S. Cl.
CPC ...... *A61B 17/0401* (2013.01); *A61B 17/0482* (2013.01); *A61B 2017/0409* (2013.01); *A61B 2017/0464* (2013.01)
(58) Field of Classification Search
CPC ............ A61B 17/0401; A61B 17/0482; A61B 2017/0409; A61B 2017/0464; A61B 17/0469
See application file for complete search history.

(56) References Cited

U.S. PATENT DOCUMENTS 5,085,661 A * 2/1992 Moss .................. A61B 17/068
606/139

* cited by examiner

*Primary Examiner* — Julian W Woo
(74) *Attorney, Agent, or Firm* — LEX IP MEISTER, PLLC

(57) ABSTRACT

A surgical instrument for repairing a cartilage tear, of the present invention, can simply and safely fix a first fixing piece (501) and a second fixing piece (502) to a torn cartilage through a very simple method for sequentially discharging the first fixing piece (501) and the second fixing piece (502) provided to be connected to suture threads (10) through a needle (411) at the tip of a push rod guide (410) while selectively moving a push rod (200) a predetermined width forward in multiple stages by means of an operation of pressing and lowering a push button (300), which is inserted into a button coupling hole (120) of an instrument body (100) so as to receive the elastic repulsive force of a spring (310), or releasing and lifting the pressed button. In addition, since the present invention definitively divides the operations of discharging the first fixing piece (501) and the second fixing piece (5020), a safety pin (600) is inserted into the push button after an operator has discharged the first fixing piece (501) so that the push button (300) is not pressed unless the push button (300) is unlocked again, thereby preventing an erroneous operatio in which the second fixing piece (502) is discharged to another position instead of the correct position by mistake.

5 Claims, 12 Drawing Sheets

SURGICAL INSTRUMENT FOR REPAIRING CARTILAGE TEAR

TECHNICAL FIELD

The present disclosure relates to a surgical instrument for repairing a cartilage tear and, more particularly, a surgical instrument for repairing a cartilage tear that uses a very simple method that sequentially protrudes a first fixing member and a second fixing member connected with a suture through the needle at the front end of the push rod guide by selectively protruding a push rod in multiple steps by predetermined distances through the operation of pressing down or releasing upward a push button inserted to receive elastic reaction force of a spring in a button coupling hole of a tool body, thereby being able to simply and safely fix the first fixing member and the second fixing member at the ruptured cartilage and being able to sew and suture the ruptured cartilage later using a suture with the first fixing member and the second fixing member for a basis so that the ruptured cartilage can be very easily repaired.

BACKGROUND ART

It is inevitability in the medical field that minimum invasive surgery or robotic surgery will be introduced and developed in the orthopedics for quick recovery of patients.

Arthroscopic surgery is the current trend for sports damage, damage to ligaments due to arthritis or degenerative diseases, or rupture of muscles in the orthopedic field and orthopedic surgery will follow this trend.

Accordingly, anchors (suture anchor) are used to bond an injured joint capsule, cartilage, muscle, ligaments, etc.

According to the surgery process, a diseased part is mini-incised or is checked through arthroscopy, the muscles or ligaments around the diseased part are fixed with sutures (e.g., fiber wire sutures), the diseased part is exposed, and a screw (anchor) with a thread is inserted therein.

A suture is attached to the anchor, so a separated ligament or muscle can be sewn and bonded to a bone. In this case, the anchor should be inserted through a cannula.

A separated or injured ligament is pulled and attached to a bone by the suture attached to the anchor and then the suture is knotted.

Such knotting should be made outside an endoscope, so knotting takes a lot of time. Further, if the suture is not accurately knotted, the suture is untied or loosened, so muscles or ligaments are not attached to a bone.

Mechanism and system related to an anchor insertion device have been disclosed, for example, in Korean Patent Nos. 10-2012-123517, 10-2014-72657, 10-2014-116211, 10-2015-7028488, etc.

However, the mechanisms and systems related to an anchor insertion device are all used only to insert and fix an anchor having a suture into a bone and attach separated ligaments or muscles to the bone by sewing them with the suture with the anchor inserted in the bone for a basis, and cannot be used to repair only a cartilage, for example, when a ligament of a knee is ruptured.

DISCLOSURE

Technical Problem

The present disclosure has been made in an effort to solve the problems described above and an objective of the present disclosure is to provide a surgical instrument for repairing a cartilage tear that uses a very simple method that sequentially protrudes a first fixing member and a second fixing member connected with a suture through the needle at the front end of the push rod guide by selectively protruding a push rod in multiple steps by predetermined distances through the operation of pressing down or releasing upward a push button inserted to receive elastic reaction force of a spring in a button coupling hole of a tool body, thereby being able to simply and safely fix the first fixing member and the second fixing member at the ruptured cartilage and being able to sew and suture the ruptured cartilage later using a suture with the first fixing member and the second fixing member, which are fixed in a ruptured cartilage rather than a bone, for a basis so that the rupture cartilage can be very easily repaired.

Technical Solution

A surgical instrument for repairing a cartilage tear of the present disclosure for achieving the objectives, fundamentally includes: a hollow tool body having a tube body coupling hole formed at a front surface, a button coupling hole formed on a top of a front portion, and a grip formed on an outer surface behind the button coupling hole;

a push rod having a rear end portion that is inserted in the tool body to receive elastic reaction force of a spring and a front end portion that protrudes forward through the tube body coupling hole;

a push button inserted in the button coupling hole of the tool body to receive elastic reaction force of a spring and coupled to and operated with the push rod to selectively move forward the push rod in multiple steps;

a push rod guide coupled to the tube body coupling hole of the tool body, surrounding an outer surface of a front end of the push rod, and having a needle having a cut portion at a front end thereof and a gauge tube body having a gauge tube holder that can selectively move forward and rearward a gauge tube surrounding an outer surface of the push rod guide.

A surgical method of repairing a cartilage tear using the surgical instrument for repairing a cartilage tear sequentially protrudes a first fixing member and a second fixing member connected with a suture through the needle at the front end of the push rod guide, includes: in order to protrude the first fixing member, a step (S1) in which a safety pin is fully inserted and fixed in the push button in an initial state, in which the push button is locked not to be pressed by the safety pin, such that the push button is enabled to be pressed for surgery;

a step (S2) in which the push button is pressed down such that the push rod blocked not to move forward by a first stopper in the push button is moved forward to a second stopper by the elastic reaction force of the spring and simultaneously the safety pin is unlocked; and a step (S3) in which when the push button moved down is released, the push button is moved up by the elastic reaction force of the spring which is compressed when the push button is pressed, the push rod is released from the second stopper, is further moved forward to a third stopper, and moves both the second fixing member and the first fixing member such that only the first fixing member protrudes out of the needle at the front end of the push rod guide to be positioned and fixed on a rear side of a partial cartilage, and the safety pin unlocked after the push button is moved up is returned rearward to an initial position by elastic reaction force of a spring such that the push button is locked not to be pressed, and includes, in order to protrude the second fixing member as a following operation, a step (S4) in which the safety pin is fully inserted and fixed again in the push button, whereby the push button is unlocked;

a step (S5) in which the push button is pressed down such that the push rod blocked not to move forward by the third stopper in the push button is moved forward by a predetermined distance by elastic compressive reaction force of the spring and the second fixing member is protruded out of the needle at the front end of the push rod guide and fixed on a rear side of another cartilage; and a step (S6) in which when the push button moved down is released, the push button is moved up by the elastic reaction force of the spring, which is compressed when the push button is pressed, and the safety pin that is unlocked is returned rearward to an initial position by elastic reaction force of the spring such that the push button is locked not to be pressed, and further includes the surgical method further comprising a step (S7) in which a suture connected to the first fixing member and the second fixing member are tied and knotted, thereby suturing a ruptured cartilage after the step (S6).

Advantageous Effects

There is an advantage that the surgical instrument for repairing a cartilage tear of the present disclosure uses a very simple method that sequentially protrudes a first fixing member and a second fixing member connected with a suture through the needle at the front end of the push rod guide by selectively protruding a push rod in multiple steps by predetermined distances through the operation of pressing down or releasing upward a push button inserted to receive elastic reaction force of a spring in a button coupling hole of a tool body, thereby being able to simply and safely fix the first fixing member and the second fixing member at the ruptured cartilage.

Accordingly, it is possible to sew and suture the ruptured cartilage later using a suture with the first fixing member and the second fixing member for a basis so that the rupture cartilage can be very easily repaired.

Further, since pressing of the push button is controlled by the safety pin that is operated with the push button, the first fixing member and the second fixing member are definitely separately protruded, so it is possible to completely prevent an operator from making misoperation of protruding the second fixing member to a wrong position by mistake.

Therefore, it is apparent that the present disclosure is a very epochal invention that can be used for surgery of safely and conveniently suture a ruptured cartilage by the above advantages.

DESCRIPTION OF DRAWINGS

FIGS. 4 to 11b are views showing the operation state of the present disclosure, in which FIG. 4 is a view showing the initial state before a surgical instrument for repairing a cartilage tear is used, FIG. 5 is a view showing the state in which a push button is unlocked and can be pressed by fully inserting and fixing a safety pin in the push button, FIG. 8 is a view showing the state in which the push button has been unlocked by inserting the safety pin into the push button to protrude a second fixing member, FIG. 9 is a view showing the state in which the unlocked push button is pressed, FIG. 11b is a view showing the state in which the safety button unlocked in the push button fully moved up by elasticity of a spring has been returned to the initial state by the elasticity of the spring and the push button has been unlocked.

Figure 1:
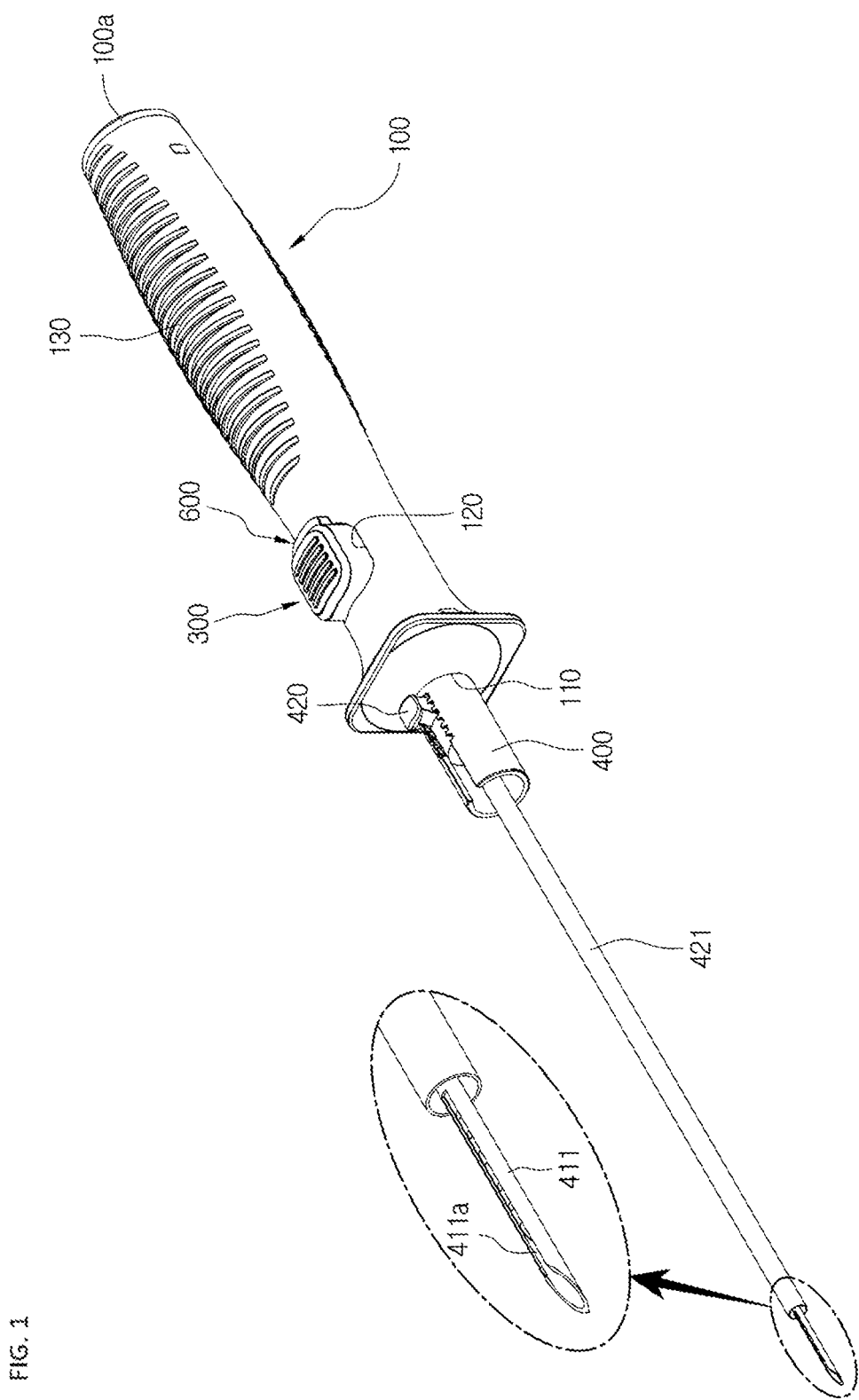
FIG. 1 is a view showing an entirely assembled state of the present disclosure.
Figure 2A:
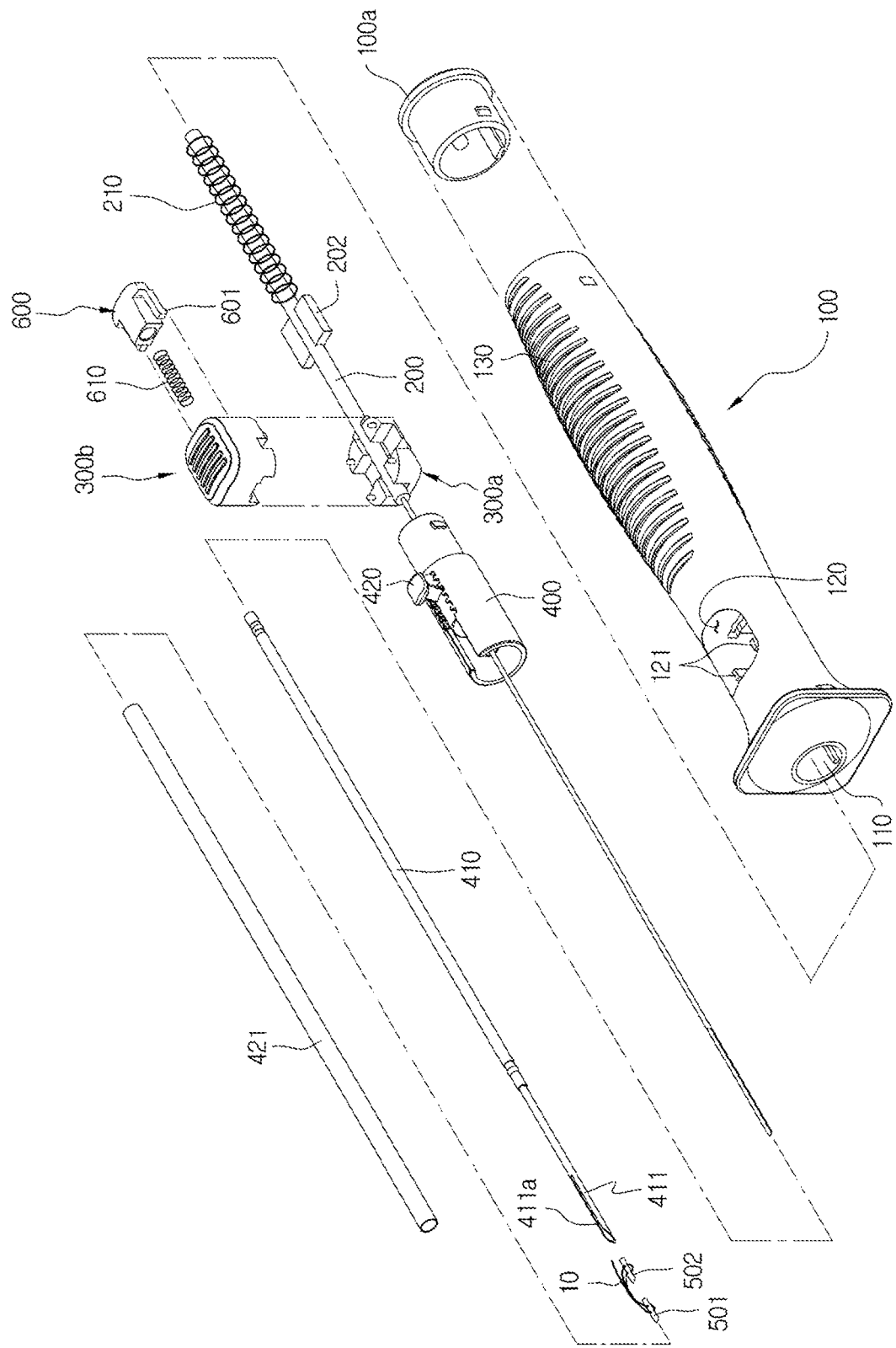
FIGS. 2a and 2b are views showing a disassembled state of main parts of the present disclosure.
Figure 2B:
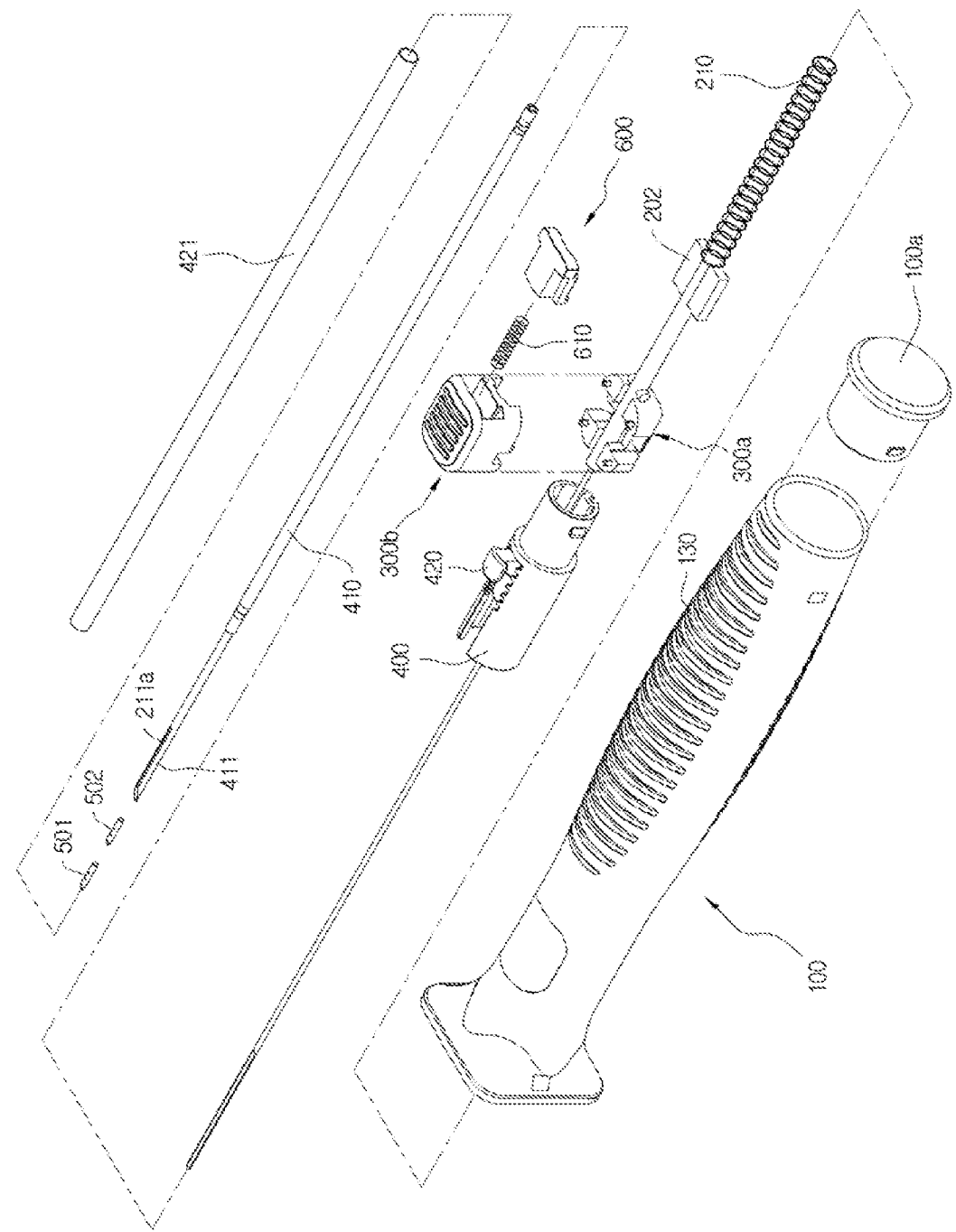
Figure 3:
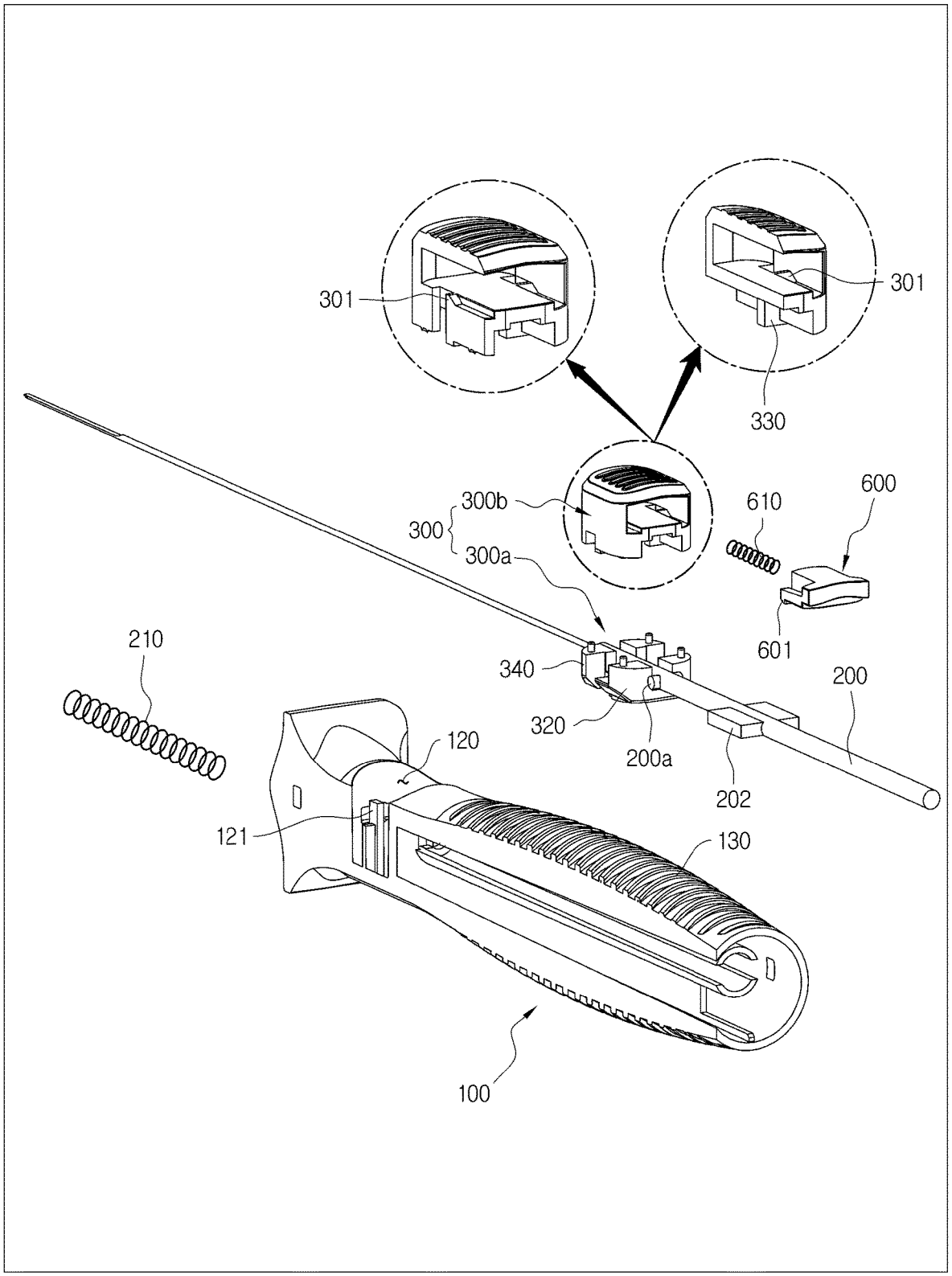
FIG. 3 is an enlarged view showing the configuration of main parts of the present disclosure.

| [Description of reference numerals] | |
|---|---|
| 10: suture | 100: tool body |
| 101, 401: wall | 110: tube body coupling hole |
| 120: button coupling hole | 121: safety release member |
| 200: push rod | 200a, 601: locking protrusion |
| 210, 310, 610: spring | 300: push button |
| 301: lockign step | 320: first stopper |
| 330: second stopper | 340: third stopper |
| 400: gauge tube body | 410: push rod guide |
| 411: needle | 411a: cut portion |
| 420: gauge tube holder | 421: gauge tube |
| 501: first fixing member | 502: second fixing member |
| 600: safety pin | |

BEST MODE

Hereafter, an embodiment of the present disclosure for achieving the objects described in the summary is described with reference to FIGS. 1 to 11b. The following embodiments are only example for helping understand the present invention and it should be understood that the present invention may be modified in various ways different from the embodiments described herein. However, in describing the present invention, detailed descriptions and drawings of well-known functions or components relating to the present disclosure will not be provided so as not to obscure the description of the present disclosure with unnecessary details. Further, the dimensions of some components are not shown with the actual scales and may be exaggerated in the drawings to help understand the present disclosure.

A surgical instrument for repairing a cartilage tear of the present disclosure, in broad meaning, includes: a hollow tool body 100 having a grip on the outer surface of the rear portion; a push rod 200 coupled to the tool body 100 and used to press forward a first fixing member 501 and a second fixing member 502; a push button 300 sequentially protruding the first fixing member 501 and the second fixing member 502 by moving the push rod 200 forward in multiple steps; and a gauge tube body 400 having a push rod guide 410 guiding the push rod 200 and having a needle 411 with a cut portion 411a at the front end.

Although the needle 411 shown in the figures is straightly formed for the convenience in the embodiment, it may be curved.

The surgical instrument for repairing a cartilage tear having the above configuration of the present disclosure is described in more detail.

First, the tool body 100 that is a hollow member has a tube body coupling hole 110 on the front surface, a button coupling hole 120 on the top of the front portion, and a grip 130 on the outer surface behind the button coupling hole 120.

A gauge tube body 500 is coupled in the tube body coupling hole 110 formed on the front of the hollow tool body 100.

The rear end portion of the push rod guide 410 that surrounds the outer surface of the front end of the push rod 200 and has the pointed needle 411 at the front with the first fixing member 501 and the second fixing member 502 inserted in the cut portion 411a formed on the top of the needle 411 is coupled to the gauge tube body 400. Further, the rear end of a gauge tube 421 surrounding the outer surface of the push rod guide 410 is coupled to the gauge tube body 400.

The rear end of the gauge tube 421 is coupled to the gauge tube holder 420 and the gauge tube holder 420 is coupled to the gauge tube body 400 to be able to selectively move forward and rearward. Accordingly, it is possible to adjust the protruding lengths of the first fixing member 501 and the second fixing member 502 in accordance with the thickness of a ruptured cartilage, that is, the conditions of the surgery part by moving forward and rearward gauge tube holder 420 such that the gauge tube 421 is simultaneously moved forward and rearward.

Meanwhile, the push rod 200 is installed in the tool body 100. The rear end portion of the push rod 200 is inserted to receive elastic reaction force of the spring 210 and the front end portion of the push rod 200 protrudes forward through the push rod guide 410 formed in the gauge tube body 400 coupled to the tube body coupling hole 110.

The push button 300 is coupled to the button coupling hole 120 of the tool body 100 to operate with the push rod 200.

For example, the push button 300 is composed of a lower button body 300a and an upper button body 300b that are separately manufactured and the integrated by an adhesive, and has a spring 310 on the bottom thereof.

The first stopper 320 and the third stopper 340 that protrude upward are formed at the lower button body 300a.

The second stopper 330 protruding downward to be positioned between the first stopper 320 and the third stopper 340 is formed at the upper button body 300b.

Therefore, according to this configuration, a locking protrusion 200a of the push rod 200 is blocked by the first stopper 320 not to move forward in the initial state.

In this state, when the push button 300 is pressed, the first stopper 320 and the second stopper 330 are both moved down, whereby the locking protrusion 200a of the push rod 200 is moved forward only to the second stopper 330 over the first stopper 320. When the push button 300 is released, the second stopper 330 and the third stopper 340 are both moved up and the locking protrusion 200a of the push rod 200 is moved to the third stopper 340 over the second stopper 330.

Accordingly, the first fixing member 501 is protruded through the needle 411 at the push guide 410 by the push rod 200 moving forward to the third stopper 340.

After the first fixing member 501 is protruded by pressing and then releasing the push button 300, when the push button 300 moved up is pressed again, the third stopper 340 is moved down, the locking protrusion 200a of the push rod 200 is moved forward over the third stopper 340 by the elastic reaction force of the spring 210, and a stepped portion 201 or a locking projection 202 formed on the push rod 200 is blocked by a wall 401 in the gauge tube body 400 or a wall 101 in the tool body 100, whereby the push rod 200 is moved only by a predetermined distance. Accordingly, the second fixing member 502 is protruded through the needle 411 at the front end of the push rod guide 410 by the push rod 200 moving forward.

The present disclosure may further include a safety pin 600 that controls pressing of the push button 300.

The front end portion of the safety pin 600 is inserted to receive elastic reaction force of a spring 610 inside the push button 300 and the rear end portion thereof further protrudes out of the button coupling hole 120 such that the push button 300 is locked by the safety pin 600 not to be pressed.

When the safety button 600 is fully inserted inside the push button in this state, locking protrusions 601 formed on both sides of the safety pin 600 are moved forward and blocked and fixed by locking steps 301 formed on both sides inside the push button 300, whereby the push button 300 is unlocked to be able to be pressed.

Safety pin release members 121 are vertically installed in the button coupling hole 120 of the tool body 100 such that the locking protrusions 601 are unlocked from the locking steps 301 by the safety release members 121 and pushed rearward by the elastic reaction force of the compressed spring 610 to release the safety pin 600 when the safety pin 600 is moved down with the locking protrusions 601 coupled and fixed to the locking steps 301 of the push button 300.

Hereafter, the operation state of the surgical instrument for repairing a cartilage tear having the above configuration of the present disclosure is described in more detail.

Figure 4:
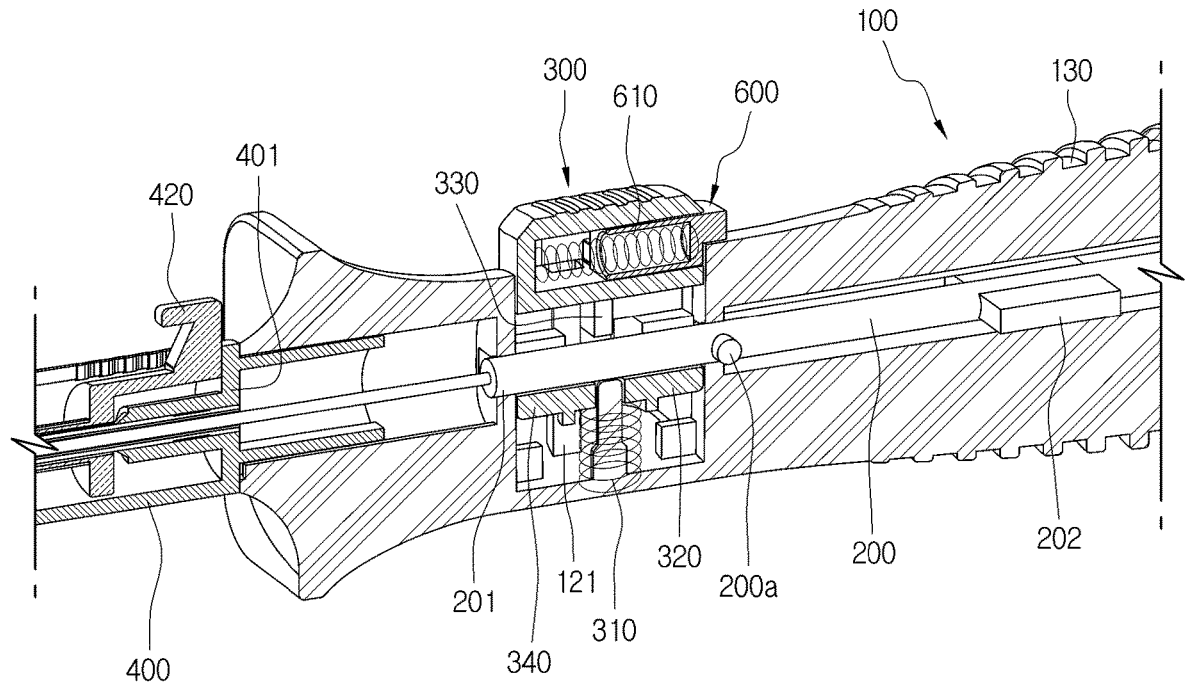

FIG. 4 shows the initial state in which the rear end portion of the safety pin 600 further protrudes out of the button coupling hole 120 with the front end inserted in the push button 300, so the push button 300 is locked and cannot be pressed by the safety pin 600.

Figure 5:
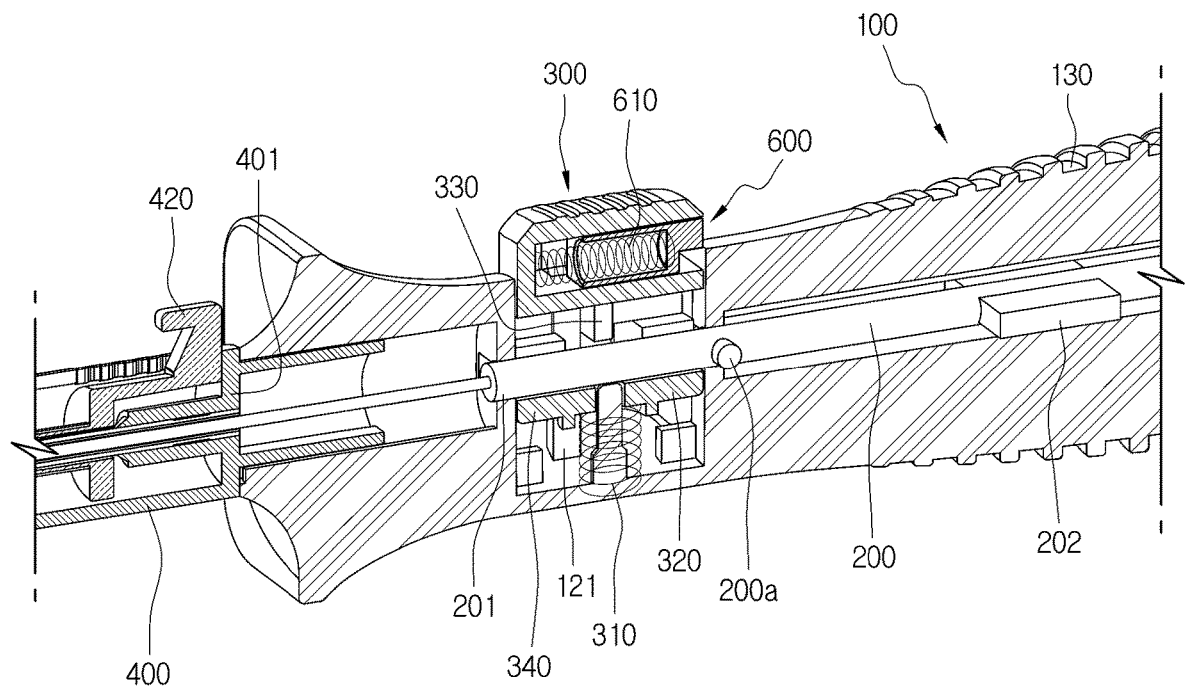

In this state, when the safety button 600 is fully inserted inside the push button for surgery, as shown in FIG. 5, the locking protrusions 601 formed on both sides of the safety pin 600 are moved forward and blocked and fixed by locking steps 301 formed on both sides inside the push button 300, whereby the push button 300 is unlocked to be able to be pressed.

In this process, the spring 610 of the safety pin 600 is compressed.

Figure 6A:
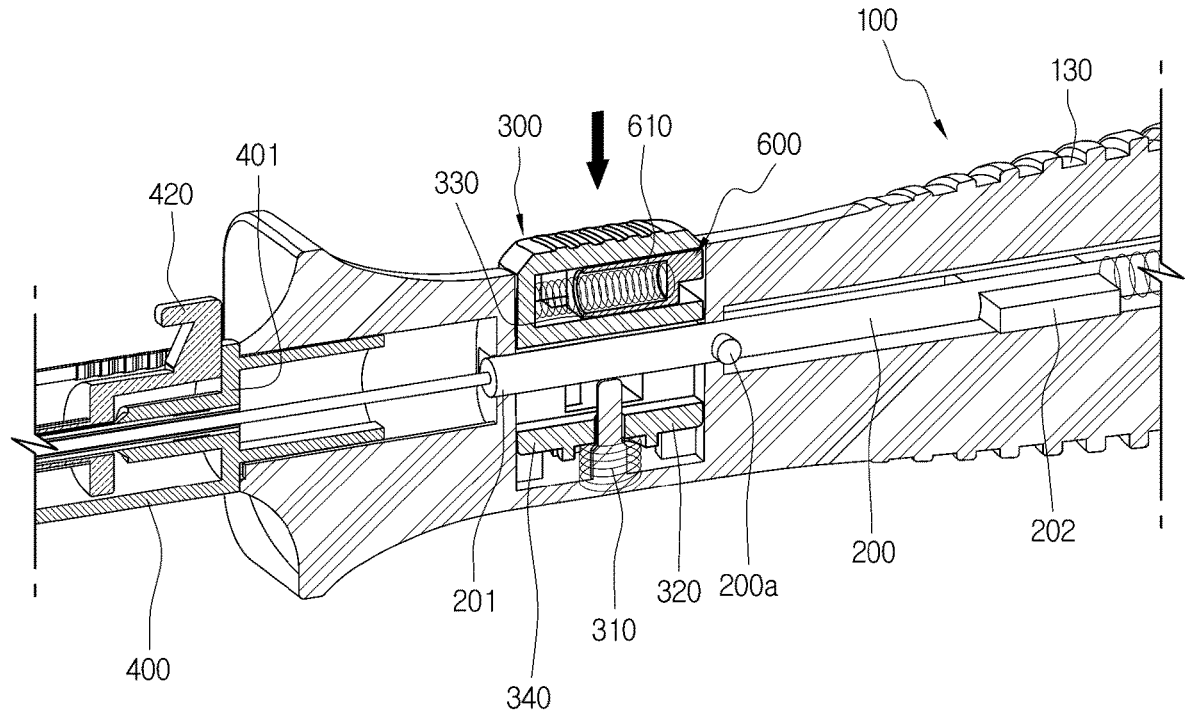
FIG. 6a is a view showing the state in which the unlocked push button is pressed.
Figure 6B:
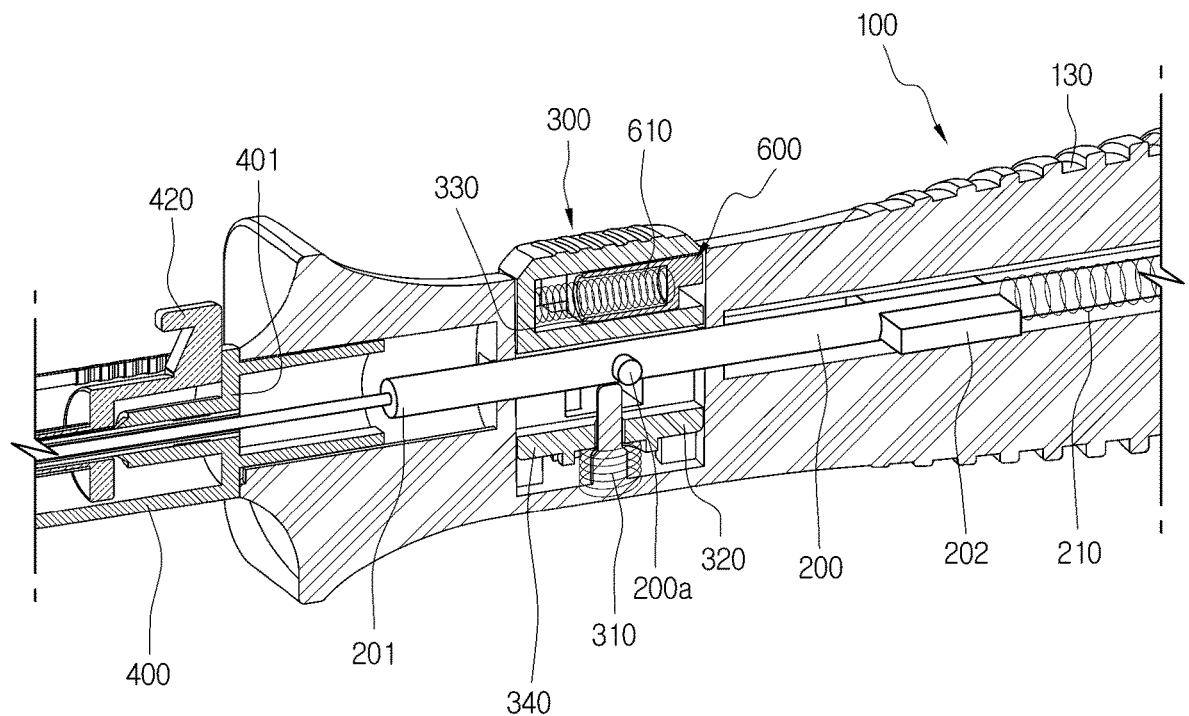
FIG. 6b is a view showing the state in which the push button has been pressed and a push rod has been moved forward to a second stopper beyond a first stopper.

Then, the push button 300 is pressed and the first stopper 320 therein is moved down, as shown in FIG. 6a, the locking protrusion 200a of the push rod 200 that is blocked by the first stopper 320 not to be moved forward is moved forward over the first stopper 320 by the elastic compressive reaction force of the spring 210 and blocked by the second stopper 330, so the locking protrusion 200a is moved only by a predetermined distance.

In this process, the bottom of the push button 300 is elastically supported by the spring 310, so the spring 310 is compressed.

Figure 6C:
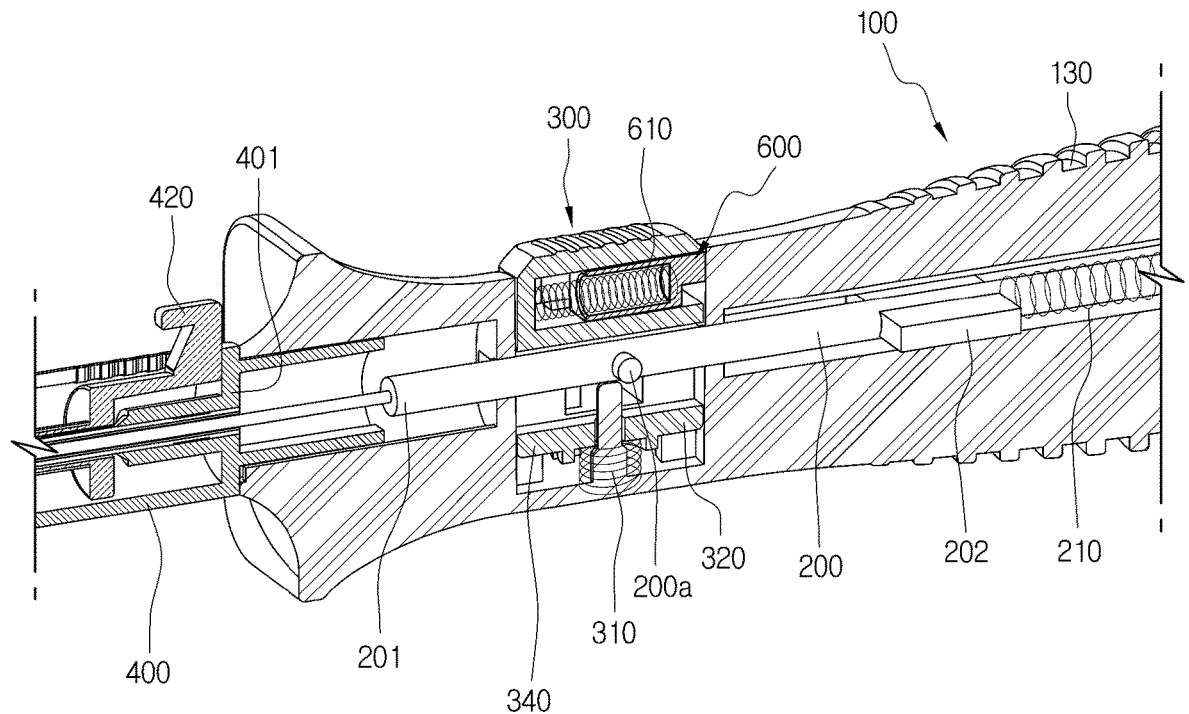
FIG. 6c is a view showing the state in which the safety pin has been unlocked.

Further, since the safety pin release members 121 are vertically installed in the button coupling hole 120 of the tool body 100, as shown in FIG. 6c, the locking protrusions 601 are unlocked from the locking steps 301 by the safety release members 121 and pushed rearward by the elastic reaction force of the compressed spring 210 when the safety pin 600 is moved down with the locking protrusion 601 coupled and fixed to the locking steps 301 of the push button 300, whereby the safety pin 600 is unlocked.

Figure 7A:
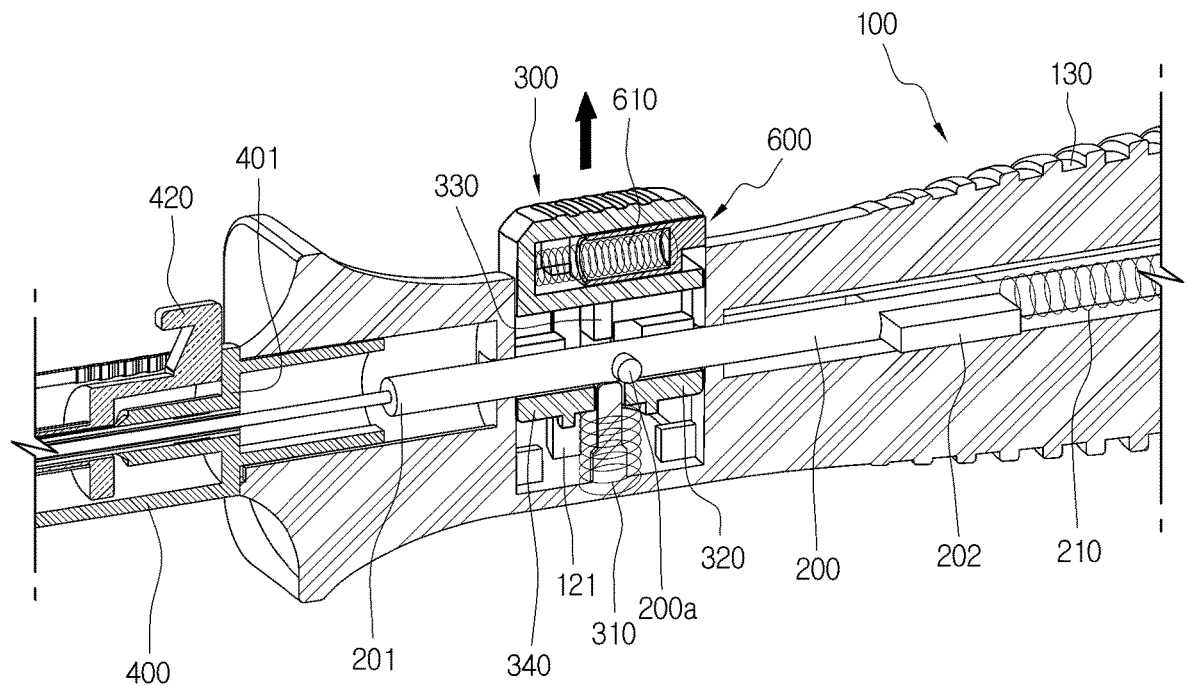
FIG. 7a is a view showing the state in which the second stopper is moved up by releasing the push button.

In this state, when the push button 300 is released, as shown in FIG. 7a, the push button 300 and the second stopper 330 in the push button 300 are both moved up by the elastic reaction force of the spring 310.

Figure 7B:
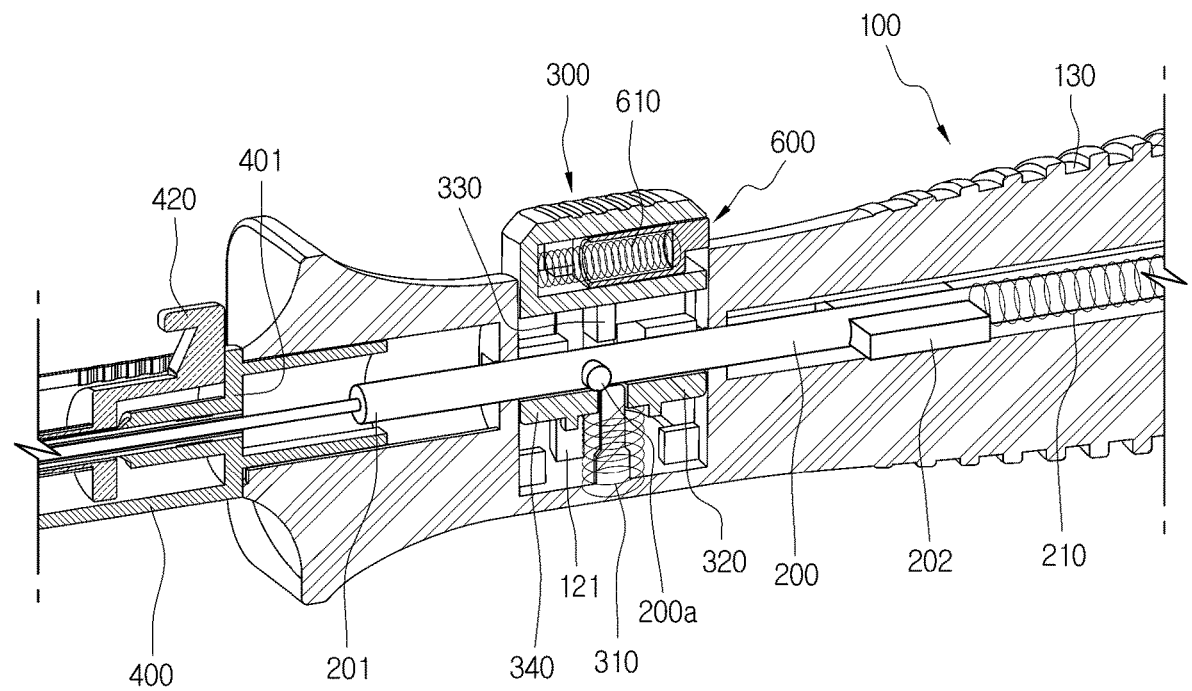
FIG. 7b is a view showing the state in which the push rod released by upward movement of the second stopper has been moved forward to a third stopper.

Accordingly, as in FIG. 7b, the locking protrusion 200a of the push rod 200 that is released by the upward movement of the second stopper 330 is moved forward to the third stopper 340.

Figure 7C:
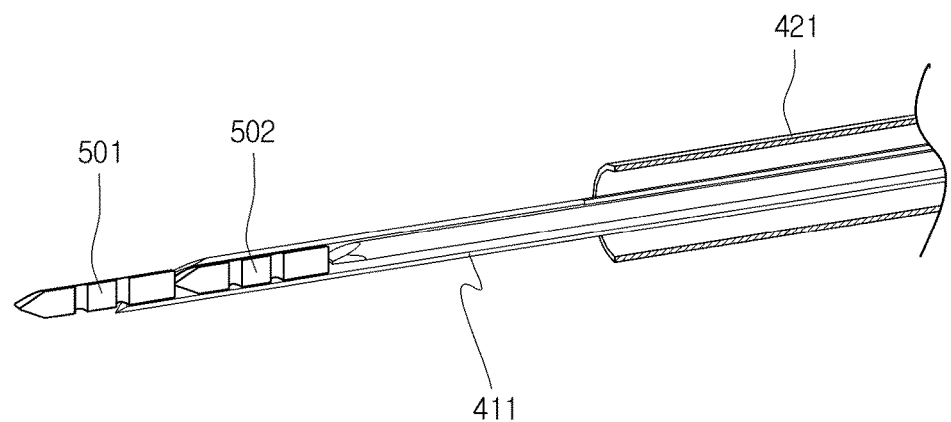
FIG. 7c is a view showing the state in which a first fixing member has been protruded by the push rod moved forward to the third stopper.
Figure 7D:
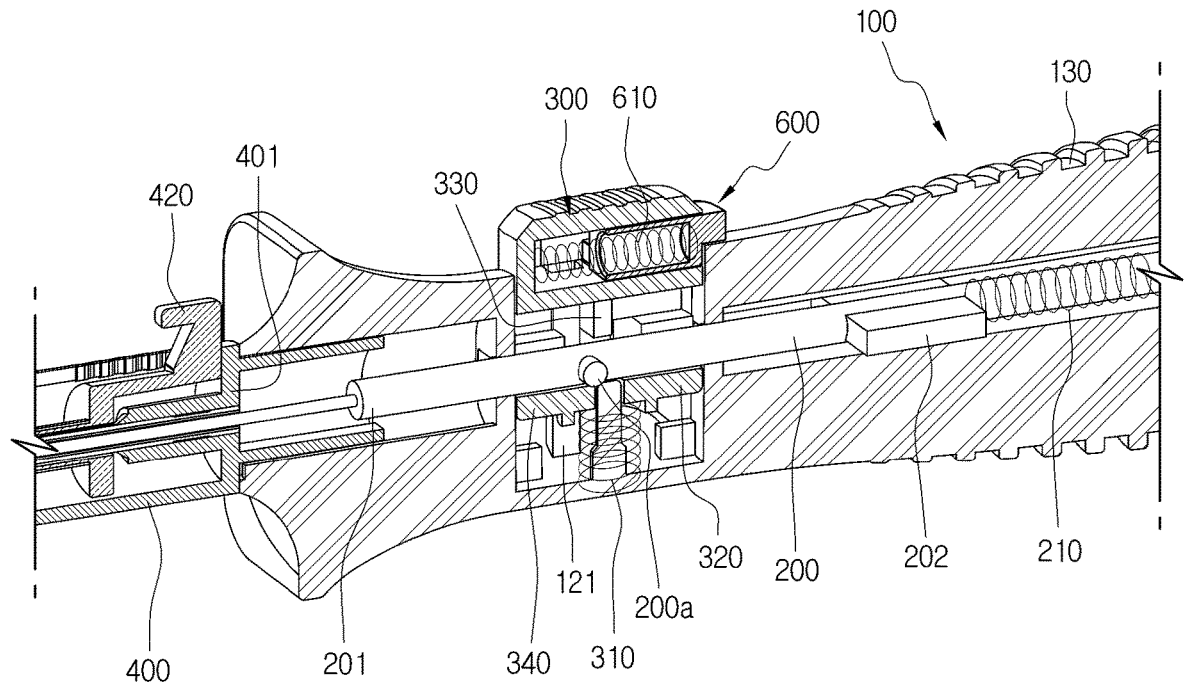
FIG. 7d is a view showing the state in which the safety button unlocked in the push button fully moved up by elasticity of a spring has been returned to the initial state by the elasticity of the spring and the push button has been unlocked.

Accordingly, as shown in FIG. 7c, the first fixing member 501 is protruded through the needle 411 at the push guide 410 by the push rod 200 moving forward to the third stopper 340.

The protruding first fixing member 501 is positioned at a rear side through a portion of a ruptured cartilage.

Further, the safety pin 600 released in the push button 300 fully moved up by the elastic reaction force of the spring 310 is returned into the initial state by the elastic reaction force of the spring 610, whereby the push button 300 is locked again.

That is, this state, as described above with reference to FIG. 4, is the initial state in which the rear end portion of the safety pin 600 further protrudes out of the button coupling hole 120 with the front end inserted in the push button 300, so the push button 300 is locked and cannot be pressed by the safety pin 600.

As described above, FIGS. 4 to 7d show a method of protruding the first fixing member 501 and a method of protruding the second fixing member 502 is described hereafter.

Figure 8:
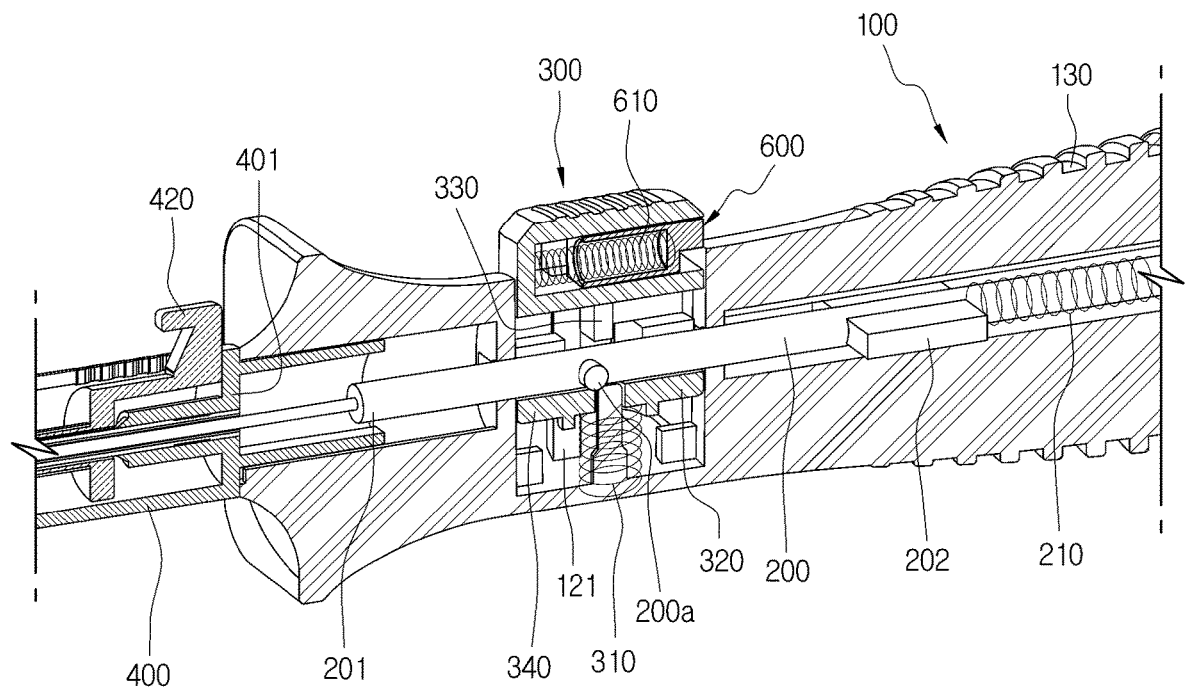

In order to protrude the second fixing member 502, as shown in FIG. 8, the safety pin 600 should be inserted back into the push button 300 to unlock the push button 300.

That is, in order to unlock the push button 300 locked by the safety pin 600, the safety pin 600 is fully inserted again into the push button 300, whereby the push button 300 is unlocked to be able to be pressed.

When the safety button 600 is fully inserted inside the push button, as described above, the locking protrusions 601 formed on both sides of the safety pin 600 are moved forward and blocked and fixed by locking steps 301 formed on both sides inside the push button 300, whereby the push button 300 is unlocked to be able to be pressed.

In this process, the spring 610 of the safety pin 600 is compressed.

Figure 9:
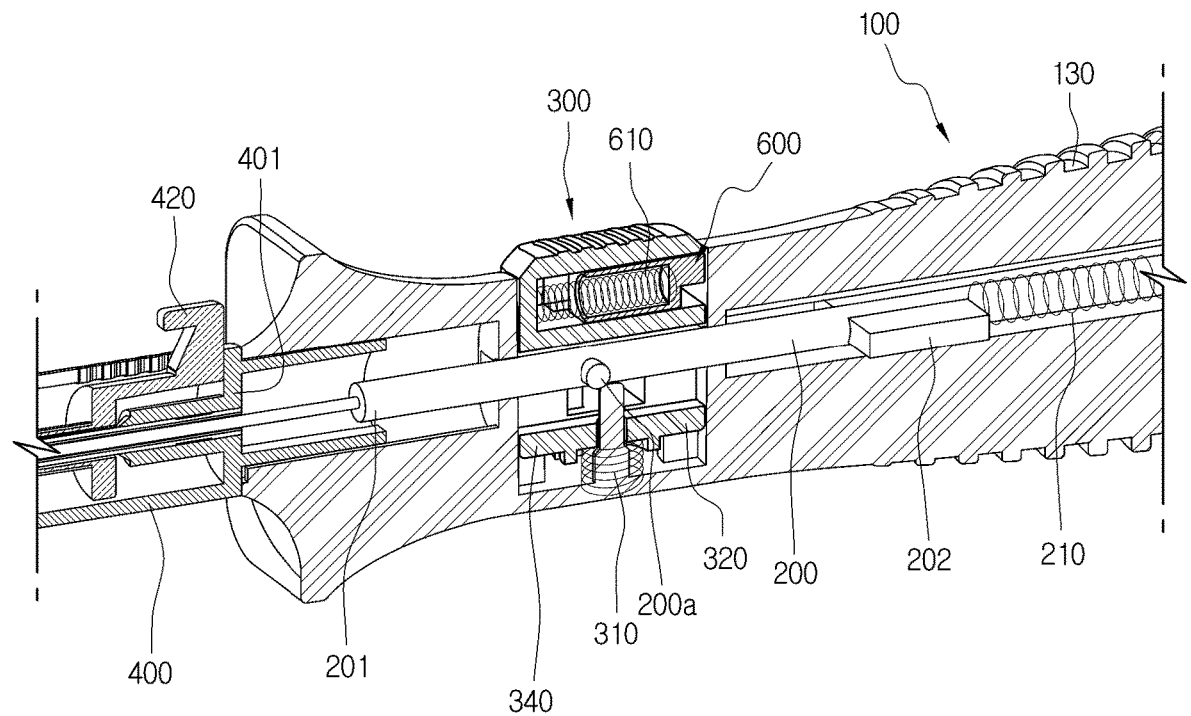

Thereafter, the unlocked push button 300 is pressed down, as shown in FIG. 9.

Figure 10A:
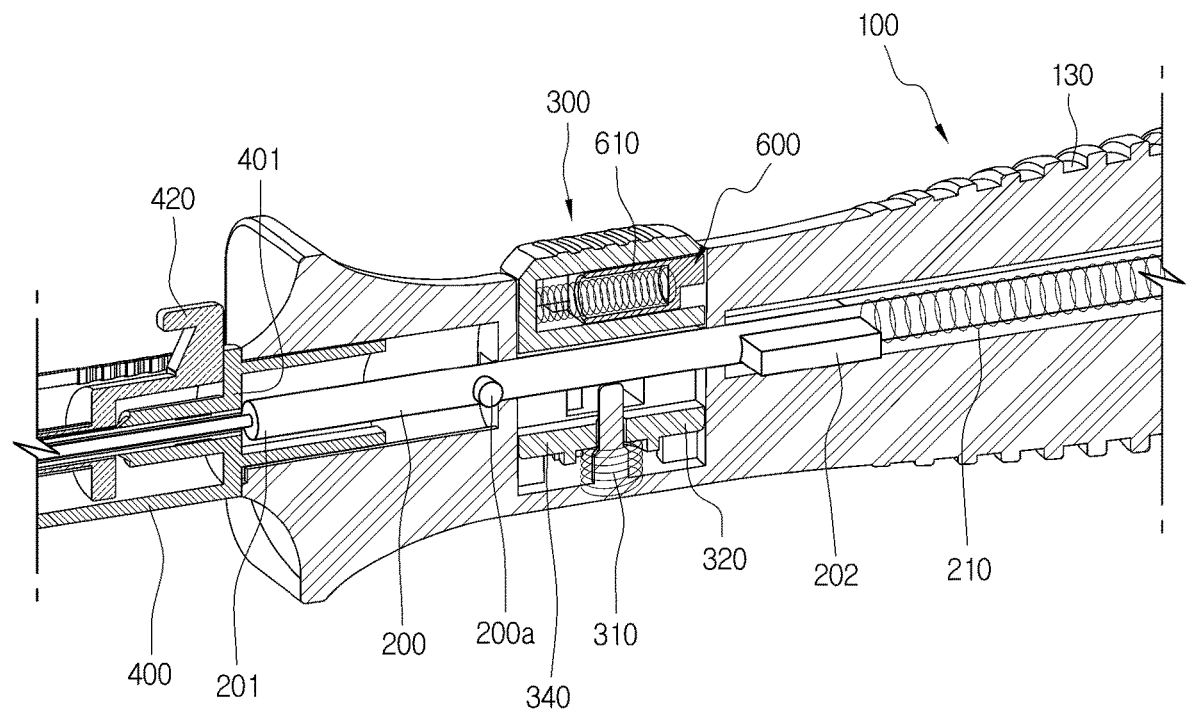
FIG. 10a is a view showing the state in which the push button has been pressed and a push rod has been moved forward to the third stopper beyond the second stopper.
Figure 10B:
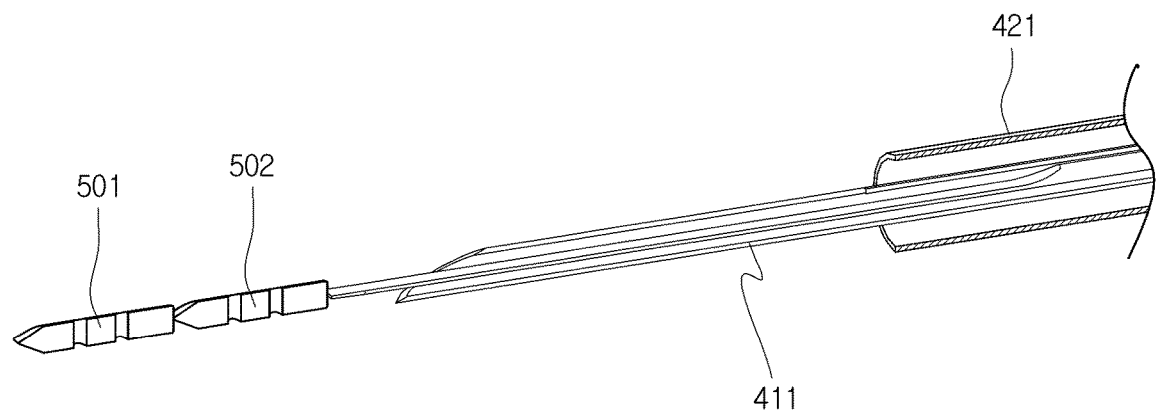
FIG. 10b is a view showing the state in which the second fixing member has been protruded by the push rod moved forward to the third stopper.

Accordingly, as shown in FIG. 10a, as the push button 300 is pressed, the third stopper 340 in the push button 300 is moved down, the locking protrusion 200a of the push rod 200 that is blocked by the third stopper 340 not to move forward is moved forward over the third stopper 340 by the elastic compressive reaction force of the spring 210, and the stepped portion 201 of the locking projection 202 of the push rod 200 is blocked by the wall 401 in the gauge tube body 400 or the wall 101 in the tool body 100, so the push road 200 is moved forward only by a predetermined distance. Accordingly, the second fixing member 502 is protruded through the needle 411 at the front end of the push rod guide 410 by the push rod 200 moving forward, as shown in FIG. 10b.

The protruding second fixing member 502 is positioned at a rear side through another portion to suture the ruptured cartilage.

The spring 310 supporting the bottom of the push button 300 is compressed when the push button 300 is moved down.

Figure 10C:
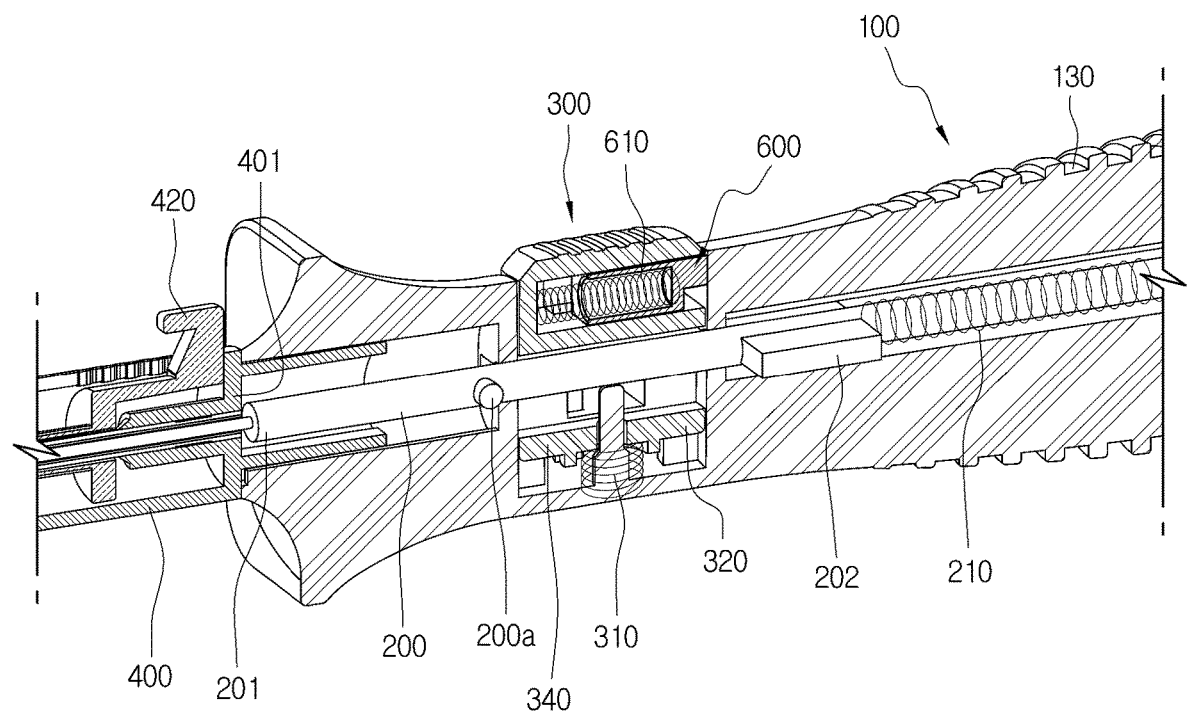
FIG. 10c is a view showing the state in which the safety pin has been unlocked.

Further, since the safety pin release members 121 are vertically installed in the button coupling hole 120 of the tool body 100, as shown in FIG. 10c, the locking protrusions 601 are unlocked from the locking steps 301 by the safety release members 121 and pushed rearward by the elastic reaction force of the compressed spring 610 when the safety pin 600 is moved down with the locking protrusion 601 coupled and fixed to the locking steps 301 of the push button 300, whereby the safety pin 600 is unlocked.

Figure 11A:
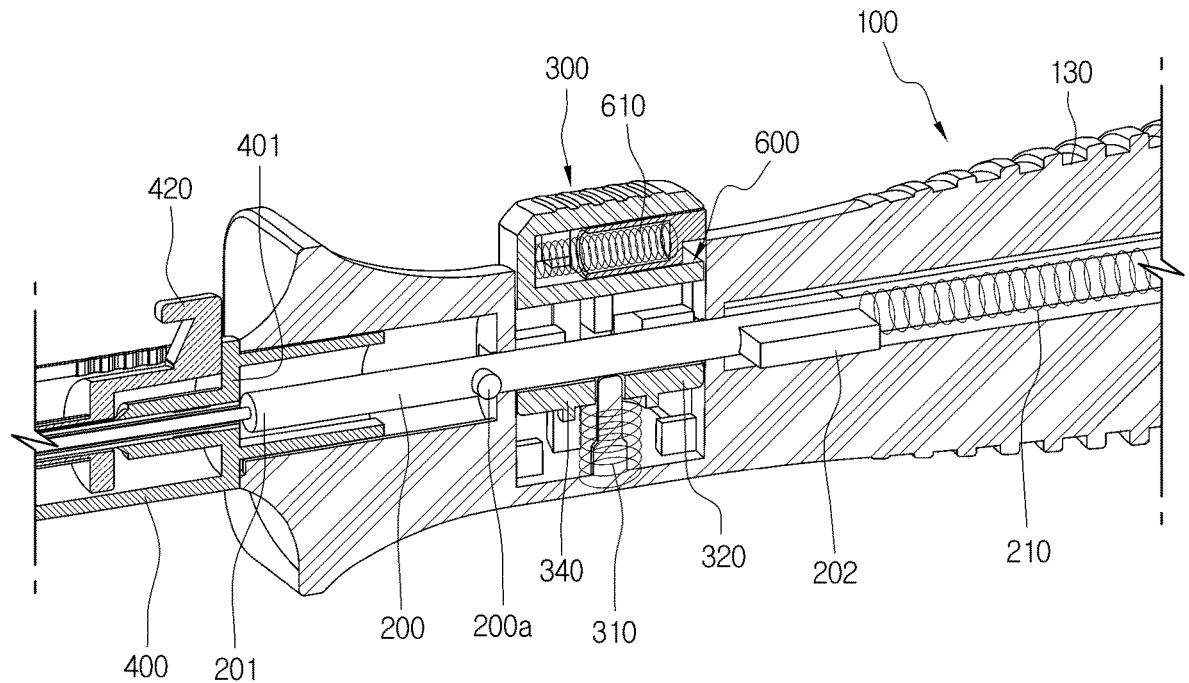
FIG. 11a is a view showing the state in which the push button has been released and moved up by the elasticity of the spring after the second fixing member is protruded.
Figure 11B:
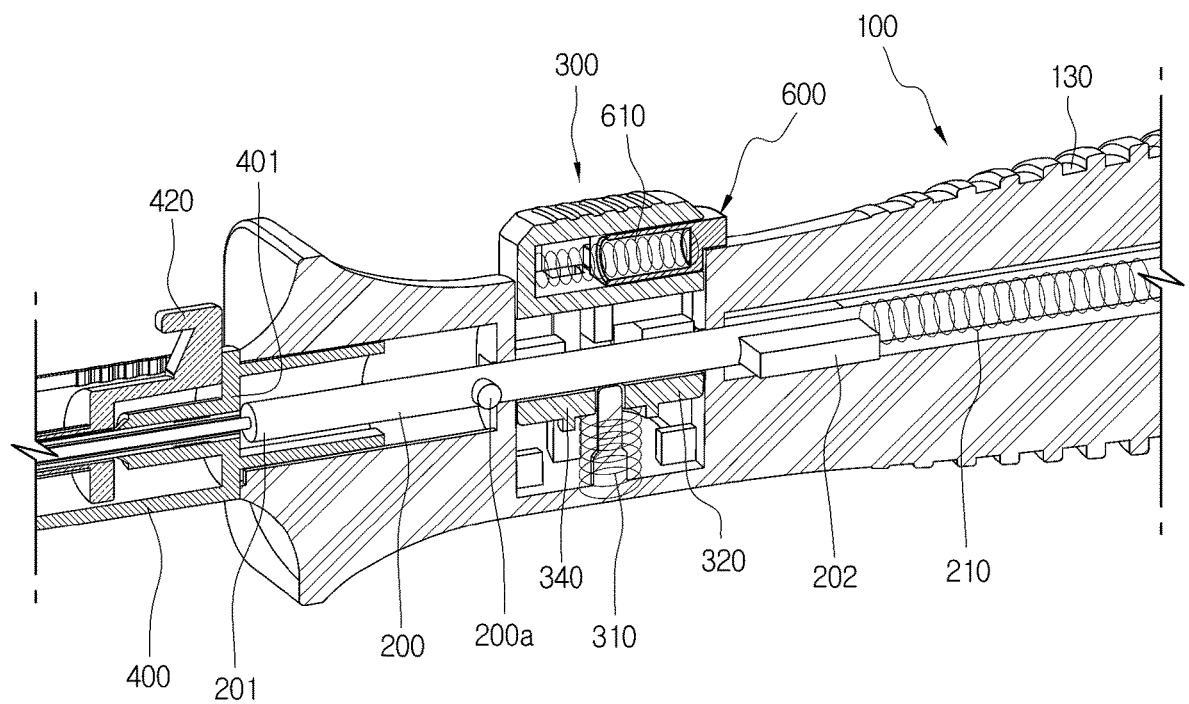

In this state, when the push button 300 is released, as shown in FIG. 11a, the push button 300 is moved up by the elastic compressive reaction force of the spring 310 compressed on the bottom of the push button 300.

When the push button 300 is fully moved up, the safety pin 600 unlocked in the push button 300 is returned into the initial state by the elastic reaction force of the spring 610, whereby the push button 300 is locked again.

After the first fixing member 501 and the second fixing member 502 are simply, quickly, and above all, safely and completely fixed on the rear side of ruptured portion to be sutured, the surgical instrument for repairing a cartilage tear of the present disclosure is removed. Thereafter, it is possible to perform general surgery such as sewing and suturing the ruptured cartilage using a suture with the first fixing member 501 and the second fixing member 502 for a basis.

By using the surgical instrument for repairing a cartilage tear of the present disclosure, it is possible to very simply suture and repair a ruptured cartilage.

As described above, the surgical instrument for repairing a cartilage tear of the present disclosure may perform a surgical method of repairing a cartilage tear which sequentially protrudes the first fixing member 501 and the second fixing member 502 connected with a suture 10 from the end of the cut portion 411a of the push rod guide 410.

The surgical method includes: in order to protrude the first fixing member 501, a step (S1) in which the safety pin 600 is fully inserted and fixed in the push button 300 in the initial state, in which the push button 300 is locked not to be pressed by the safety pin 600, such that the push button 300 is enabled to be pressed for surgery;

a step (S2) in which the push button 300 is pressed down such that the push rod 200 blocked not to move forward by the first stopper 320 in the push button 300 is moved forward to the second stopper 330 by the elastic reaction force of the spring 210 and simultaneously the safety pin 600 is unlocked; and a step (S3) in which when the push button 300 moved down is released, the push button 300 is moved up by the elastic reaction force of the spring 310, which is compressed when the push button 300 is pressed, the push rod 200 is released from the second stopper 330, is further moved forward to the third stopper 340, and moves both the second fixing member 502 and the first fixing member 501 such that only the first fixing member 501 protrudes out of the needle 411 at the front end of the push rod guide 410 to be positioned and fixed on the rear side of a partial cartilage, and the safety pin 600 unlocked after the push button 300 is moved up is returned rearward to the initial position by the elastic reaction force of the spring 610 such that the push button 300 is locked not to be pressed.

The method further includes: in order to protrude the second fixing member 502 as a following operation, a step (S4) in which the safety pin 600 is fully inserted and fixed again in the push button 300, whereby the push button 300 is unlocked;

a step (S5) in which the push button 300 is pressed down such that the push rod 200 blocked not to move forward by the third stopper 340 in the push button 300 is moved forward by a predetermined distance by the elastic compressive reaction force of the spring 210 and the second fixing member 502 is protruded out of the needle 411 at the front end of the push rod guide 410 and fixed on a rear side of another partial cartilage; and a step (S6) in which when the push button 300 moved down is released, the push button 300 is moved up by the elastic reaction force of the spring 310, which is compressed when the push button 300 is pressed, and the safety pin 600 that is unlocked is returned rearward to the initial position by the elastic reaction force of the spring 610 such that the push button 300 is locked not to be pressed.

The surgical method further includes a step in which the surgical instrument for repairing a cartilage tear of the present disclosure is removed and then the ruptured cartilage is sutured by tying and knotting the suture 10 with the first fixing member 501 and the second fixing member 502 for a basis.

The surgical method of repairing a cartilage tear using the surgical instrument for repairing a cartilage tear is a very simple method that sequentially protrudes the first fixing member 501 and the second fixing member 502 connected with the suture 10 through the needle 411 at the front end of the push rod guide 410 by selectively protruding the push rod 200 in multiple steps by predetermined distances through the operation of pressing down or releasing upward the push button 300 inserted to receive elastic reaction force of the spring 310 in the button coupling hole 120 of the tool body 100. Accordingly, it is possible to simply and safely fix the first fixing member 501 and the second fixing member 502 at the ruptured cartilage.

Accordingly, it is possible to sew and suture the ruptured cartilage later using the suture 100 with the first fixing member 501 and the second fixing member 502 for a basis so that the rupture cartilage can be very easily repaired.

Further, since pressing of the push button 300 is controlled by the safety pin 600 that is operated with the push button 300, the first fixing member 501 and the second fixing member 502 are definitely separately protruded, so the push button 300 is not pressed again unless an operator unlocks the push button 300 by inserting the safety pin 600 into the push button after protruding the first fixing member 501. Accordingly, it is possible to completely prevent misoperation of protruding the second fixing member 502 to a wrong position by mistake.

Although the present disclosure was described with reference to limited exemplary embodiments and drawings, the present disclosure is not limited thereto and may be changed and modified in various ways within the spirit of the present disclosure and claims described below by those skilled in the art.

INDUSTRIAL APPLICABILITY

The surgical instrument for repairing a cartilage tear of the present disclosure can be used to repair a cartilage by sewing and suturing a ruptured cartilage with a suture.

The invention claimed is:

1. A surgical instrument for repairing a cartilage tear, comprising:
    a hollow tool body (100) having a tube body coupling hole (110) formed at a front surface, a button coupling hole (120) formed on a top of a front portion, and a grip (130) formed on an outer surface behind the button coupling hole (120);
    a push rod (200) having a rear end portion that is inserted in the tool body (100) to receive an elastic reaction force of a spring (210) and a front end portion that protrudes forward through the tube body coupling hole (110);
    a push button (300) inserted in the button coupling hole (120) of the tool body (100) to receive an elastic reaction force of a spring (310) and coupled to and operated with the push rod (200) to selectively move forward the push rod (200) in multiple steps;
    a push rod guide (410) coupled to the tube body coupling hole (110) of the tool body (100), surrounding an outer surface of a front end of the push rod (200), and having a needle (411) having a cut portion (411a) at a front end thereof; and
    a gauge tube body (400) having a gauge tube holder (420) that can selectively move forward and rearward a gauge tube (421) surrounding an outer surface of the push rod guide (410).

2. The surgical instrument of claim 1, wherein the push button (300) is composed of a lower body (300a) and an upper body (300b) integrated to each other, and a first stopper (320) and a third stopper (340) that protrude upward are formed at front and rear portions of the lower body (300a);
    a second stopper (330) protruding downward to be positioned between the first stopper (320) and the third stopper (340) is formed at the upper body (300b);
    a locking protrusion (200a) of the push rod (200) is blocked by the first stopper (320) is configured not to move forward in an initial state; wherein,
    when the push button (300) is pressed, the first stopper (320) and the second stopper (330) are both moved down, whereby the locking protrusion (200a) of the push rod (200) is moved forward only to the second stopper (330) over the first stopper (320), and wherein, when the push button (300) is released, the second stopper (330) and the third stopper (340) are both moved up, the locking protrusion (200a) of the push rod (200) is moved to the third stopper (340) over the second stopper (330), and a first fixing member (501) protrudes through the needle (411) at the front end of the push rod guide (410); and wherein, when the push button (300) fully moved up is pressed again, the third stopper (340) is moved down, the locking protrusion (200a) of the push rod (200) is moved forward over the third stopper (340) by elastic compressive reaction force of the spring (210), and a stepped portion (201) or a locking projection (202) formed on the push rod (200) is blocked by a wall (401) in the gauge tube body (400) or a wall (101) in the tool body (100), whereby the push rod (200) is moved only by a predetermined distance and the second fixing member (502) protrudes through the needle (411) at the front end of the push rod guide (410).

3. The surgical instrument of claim 1, further comprising a safety pin (600) that controls pressing of the push button (300).

4. The surgical instrument of claim 3, wherein the safety pin (600) has a front end portion inserted in the push button (300) to receive an elastic reaction force of a spring and a rear end portion further protruding out of the button coupling hole (120); wherein the push button (300) is locked and cannot be pressed by the safety pin (600) normal times; and wherein, when the safety pin (600) is fully inserted inside the push button (300), locking protrusions (601) formed on both sides of the safety pin (600) are moved forward and blocked and fixed by locking steps (301) formed on both sides inside the push button (300), whereby the push button (300) is unlocked to be able to be pressed.

5. The surgical instrument of claim 4, wherein the safety pin (600) has safety pin release members (121) that are vertically installed in the button coupling hole (120) of the tool body (100) such that the locking protrusions (601) are unlocked from the locking steps (301) by the safety pin release members (121) and pushed rearward by the elastic reaction force of the compressed spring (610) to release the safety pin (600) when the safety pin (600) is moved down with the locking protrusions (601) coupled and fixed to the locking steps (301) of the push button (300).

* * * * *